(12) United States Patent
Ghelman et al.

(10) Patent No.: US 8,795,603 B2
(45) Date of Patent: Aug. 5, 2014

(54) CASSETTE FOR VACUUM AND STEAM STERILIZATION APPARATUS

(75) Inventors: Eduardo C. Ghelman, Etobicoke (CA); Neil McPhail, Vancouver (CA); Adam Szczurowski, Pickering (CA); Xiang Dong Yin, North York (CA); Edward Kitaura, Markham (CA)

(73) Assignee: SciCan, a division of Lux and Zwingenberger Ltd., Toronto, Ontario (CA)

( * ) Notice: Subject to any disclaimer, the term of this patent is extended or adjusted under 35 U.S.C. 154(b) by 0 days.

(21) Appl. No.: 13/097,230

(22) Filed: Apr. 29, 2011

(65) Prior Publication Data

US 2011/0262301 A1 Oct. 27, 2011

Related U.S. Application Data

(63) Continuation of application No. 09/958,036, filed as application No. PCT/CA00/00376 on Apr. 6, 2000, now abandoned.

(30) Foreign Application Priority Data

Apr. 6, 1999 (CA) .................................... 2268042

(51) Int. Cl.
*A61L 2/07* (2006.01)
(52) U.S. Cl.
USPC ............................. 422/292; 422/295; 277/650
(58) Field of Classification Search
USPC ............. 422/26, 292, 295, 296, 300; 277/650
See application file for complete search history.

(56) References Cited

U.S. PATENT DOCUMENTS

| | | | |
|---|---|---|---|
| 1,746,522 A | 2/1930 | Carleton |
| 2,258,746 A | 10/1941 | Dickman |
| 2,868,616 A | 1/1959 | Poitras |
| 3,086,263 A | 4/1963 | Johann |
| 3,834,872 A | 9/1974 | Joslyn |
| 4,105,407 A | 8/1978 | Sanderson |
| 4,759,909 A | 7/1988 | Joslyn |
| 4,783,321 A | 11/1988 | Spence |
| 5,145,642 A | 9/1992 | Feathers, III |
| 5,160,700 A | 11/1992 | Anderson |
| 5,266,275 A | 11/1993 | Faddis |
| 5,271,893 A | 12/1993 | Newman |
| 5,344,622 A | 9/1994 | Faddis et al. |
| 5,368,821 A | 11/1994 | Schmoegner et al. |
| 5,543,119 A | 8/1996 | Sutter et al. |
| 5,571,476 A | 11/1996 | Newman |
| 5,759,502 A | 6/1998 | Spencer et al. |

FOREIGN PATENT DOCUMENTS

| | | |
|---|---|---|
| CA | 2268042 | 10/2000 |
| DE | 19714298 | 4/1997 |

*Primary Examiner* — Sean E Conley
(74) *Attorney, Agent, or Firm* — Clark & Brody

(57) ABSTRACT

A cassette for steam sterilizing of instruments comprises a lid and a tray, the tray having an inlet and an outlet for the cassette for communication with a sterilization apparatus, and the lid having a seal configured to interface with the tray to maintain either pressure or vacuum conditions for an interior of the cassette. The seal is configured to allow the lid to move between a vacuum position and a pressurized position without exposing the cassette interior to an outside environment. The inlet and outlets have two sets of valves and seals that ensure that the cassette interior remains sterile after the sterilization process is complete and during cassette storage. One set of valves also allows access to the cassette interior for the steam sterilization cycle.

16 Claims, 9 Drawing Sheets

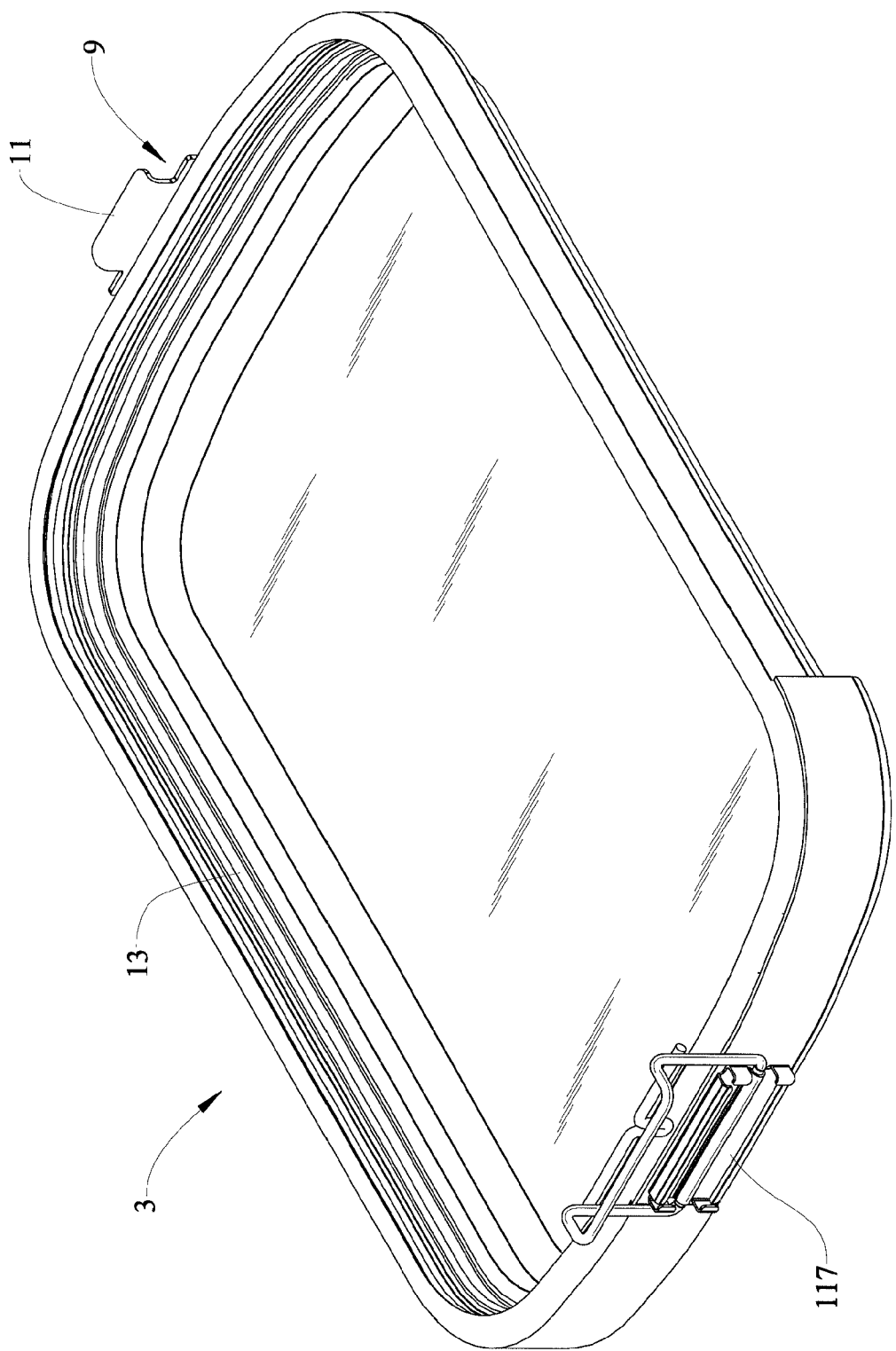

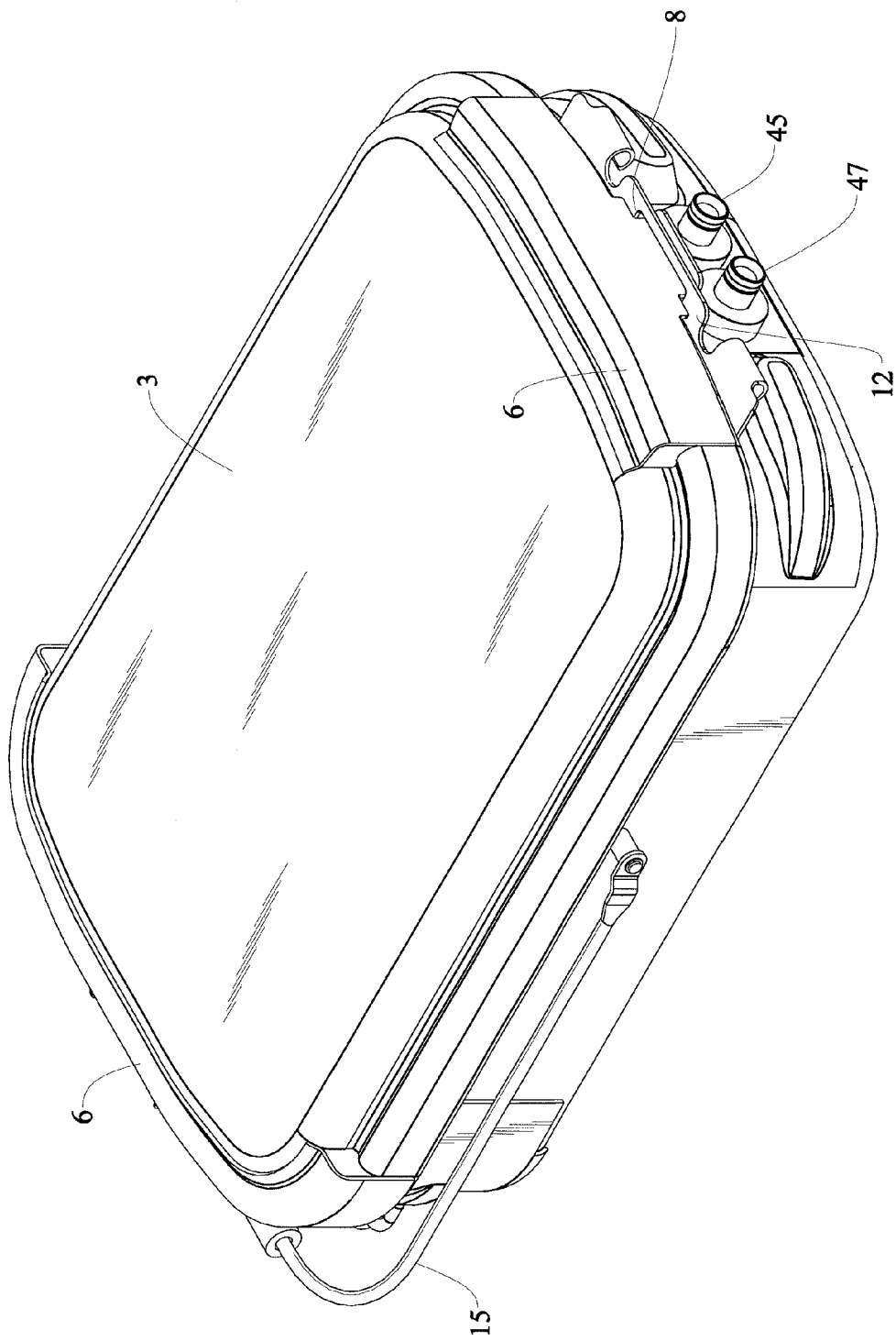

P1 > P2
A1 > A2
P1*A1+FS > P2*A2

A3 > A4
P1*A3+FS > P1*A4

A = Surface Area
P = Pressure
FS = Spring Force

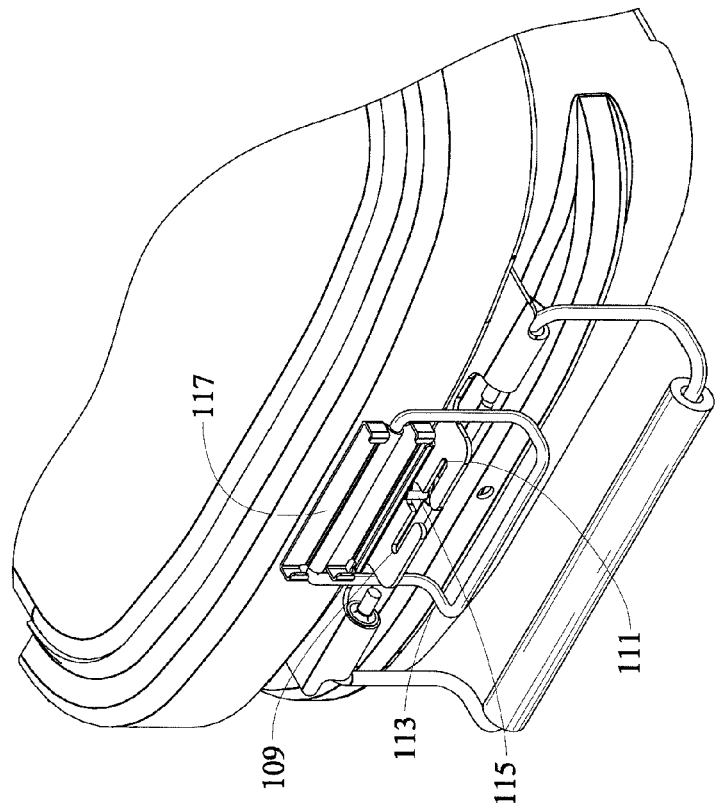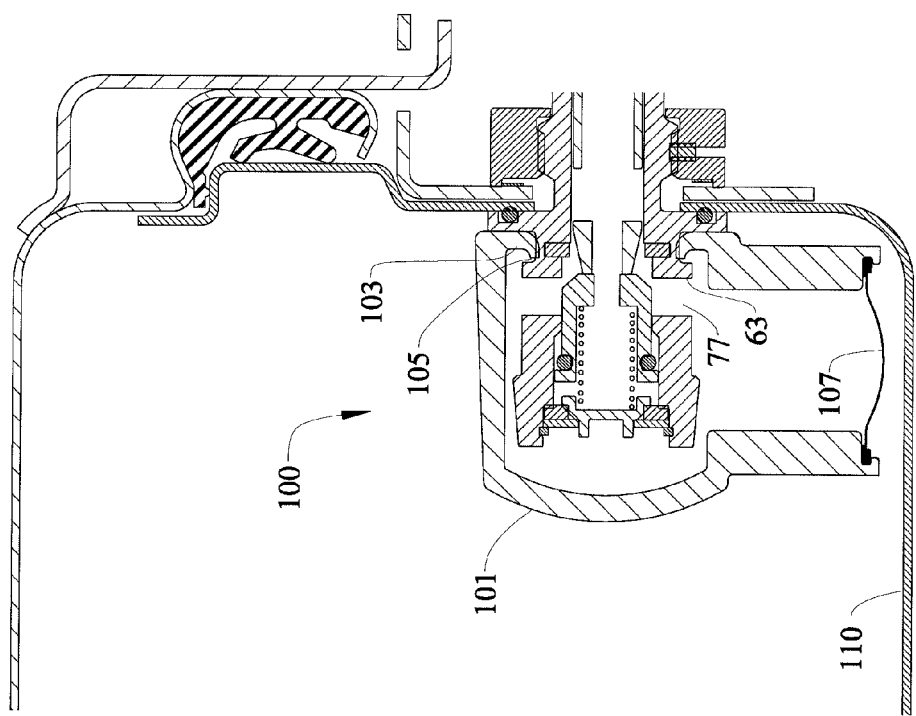

CASSETTE FOR VACUUM AND STEAM STERILIZATION APPARATUS

FIELD OF THE INVENTION

The present invention is directed to a cassette adapted for sterilizing instruments using both vacuum and steam, and in particular to a cassette having a seal allowing the cassette to operate between conditions of vacuum and pressure, and inlet and outlet couplings that facilitate sterilization as well as maintain sterility and vacuum conditions after sterilization.

BACKGROUND ART

In the prior art, various methods and apparatus have been proposed for the sterilization of medical and dental instruments. In general, these sterilization techniques use steam and/or a vacuum to purge the air from a chamber containing articles to be sterilized and steam to heat the load for sterilization. One way such sterilizations are performed is through the use of autoclaves. One type of an autoclave is a relatively large sealed vessel which contains a quantity of boiling water under pressure. The boiling water is used to purge air from the interior of the vessel. In other autoclaves, vacuum is also used for purging. In either instance, problems can develop through imperfect air purgings, and build-up of contaminants from the instruments on the walls of the autoclaves. These autoclaves are also inherently slow in sterilizing due to the large heat capacity of their heavy walls and support structures.

The apparatus disclosed in U.S. Pat. Nos. 5,271,893, 5,290,511 and 5,571,476 to Newman (hereby incorporated by reference in their entirety) overcome many of the disadvantages of conventional autoclaves. These patents disclose a steam purging and sterilization method and apparatus that employ a cassette for sterilization. Through use of the cassette, no transfer from the interior of a sterilization chamber to an auxiliary carrying tray or other post-sterilization handling, of the kind necessary with conventional autoclaves, is involved. The Newman patents also employ a small lightweight unit that is readily adapted for use in an office environment.

While the cassette-using apparatus taught by the Newman patents offer significant advantages over conventional steam purging/sterilizing autoclave techniques, these cassettes are not adapted to use vacuum as part of the steam sterilization process. In addition, these cassettes are not-designed for storing sterilized instruments.

Further, regardless of the apparatus and methods being employed, there is an ever-increasing demand for shorter steam sterilization cycles in the industry.

As such, there is a need for improved sterilization equipment for use in sterilization apparatus and methods, and particularly, equipment enabling faster sterilization times. The present invention responds to these needs by providing a cassette for use in a sterilization method and apparatus employing both vacuum and steam and one that is adapted to store sterilized instruments over time.

SUMMARY OF THE INVENTION

It is a first object of the present invention to provide a cassette adapted for use with steam sterilizing apparatus and methods that utilize conditions of vacuum and pressure. Another object of the present invention is a cassette designed to maintain sterile conditions for storage of steam-sterilized instruments.

Yet another object of the present invention is a cassette having a seal that permits the cassette to function under conditions of pressure and vacuum during a sterilization method.

Other objects and advantages of the present invention will become apparent as a description thereof proceeds.

In satisfaction of the foregoing objects and advantages, the present invention provides a sterilization cassette comprising a tray having an inlet and an outlet for connection to probes of a steam sterilization apparatus that is adapted to sterilize instruments supported by the base. The cassette has a lid hinged to the base, the lid including a seal arranged along a lid periphery. The lid is adapted to move between an open position, a closed position, and an intermediate position, the lid, the seal, and the tray forming a chamber for sterilization when the lid is in- the closed and intermediate positions.

Each of the inlet and the outlet has a first valve to permit communication between the steam sterilization apparatus and the sterilization chamber. A second valve is provided as part of the cassette to release excess pressure in the sterilization chamber. The first and second valves also seal the sterilization chamber for storage of sterilized instruments.

In one embodiment, the seal comprises a continuous seal body running along a periphery of the lid, with first and second lips extending from the seal body and being pivotally linked thereto. A third lip extends from the seal body and is spaced from the-second lip to form a channel therebetween. The first and second lips in concert with the channel provide sealing in the intermediate position and the first, second, and third lips provide sealing in the closed position.

The outlet has at least one opening positioned in the chamber, the at least one opening spaced from a bottom of the tray. A duct can be attached to the outlet at the one end thereof, with an opposite end of the duct positioned adjacent to the bottom of the tray to provide a channel for collection of condensate during steam sterilization of the instruments.

In yet another aspect of the invention, each of the inlet and the outlet further comprises a coupling body and seal assembly movably mounted through a wall of the tray to accommodate self alignment between probes of the sterilization apparatus and the coupling body while maintaining a seal between the coupling body and the wall.

The cassette also employs a unique seal to maintain sterility when the cassette is removed. In this embodiment, one end of the coupling body is arranged outside of the sterilization chamber, and a second end is arranged within the sterilization chamber. The one end has a seal device on a peripheral surface thereof. The seal device is spaced from the wall such that a seal is formed between the peripheral surface and a probe surface prior to opening or closing of the first valve to seal the sterilization chamber from ambient. In another embodiment, the cassette employs a dual valve coupling arrangement, whereby the first and second valves are arranged in the coupling body. The first valve is biased in a closed position, and adapted to be opened when a force is applied to a valve face against the bias. The second valve is biased in a closed position and movable to an open position upon application of a force applied from within the sterilization chamber. The bias can be provided by a spring arranged between the two valves. The first valve may have a bore therein that provides communication between the first opening and the second valve so that when the sterilization chamber is under a vacuum for storage, the spring bias and atmospheric pressure maintains each of the first valve and the second valve in the closed position.

The invention also entails the flexible seal for a sterilization cassette as well as a method of using the cassette as part of a sterilization process employing steam and vacuum. The method of steam sterilizing instruments comprises the steps of placing instruments in the sterilization chamber and connecting the inlet and outlet thereof to probes of a steam sterilization apparatus. The instruments are subjected to a steam sterilization cycle using pressure and vacuum conditions. The cassette is then removed upon completion of the steam sterilization cycle and is either stored with the instruments in the cassette under vacuum conditions, or the instruments are removed from the cassette for use.

The invention also includes the dual valve coupling that could be employed in other cassette designs.

BRIEF DESCRIPTION OF THE DRAWINGS

Reference is now made to the drawings of the invention wherein:

FIG. 2 is a perspective view of the lid of the cassette of FIG. 1 with portions removed for clarity;

FIG. 5 is a rear perspective view of the cassette of FIG. 1;

FIG. 10 is a partial cross sectional view of another embodiment of the coupling of the invention; and FIG. 11 is a partial front perspective view of the cassette of FIG. 1 showing an interlocking mechanism between the lid and the tray.

DESCRIPTION OF THE PREFERRED EMBODIMENTS

The inventive cassette offers significant advantages in the field of sterilizing instruments such as those used in the medical and dental fields. First, due to the unique seal of the cassette, the cassette can be used in methods and apparatus that employ vacuum conditions to remove air from the cassette prior to steam sterilization as well as the pressure conditions commonly encountered during steam sterilization.

Second, the inventive cassette permits the sterilized instruments to be stored within the cassette until ready for use. Thus, the cassette itself functions not only as a sterilizing device but also a storage device for sterilized instruments.

Third, the cassette's design also maintains a sterile atmosphere within the cassette interior when being removed from the sterilizing apparatus.

It should be understood that the inventive cassette is adapted for use with an apparatus and method that uses both vacuum and steam as part of the sterilization. More particularly, the cassette has a lid and seal assembly which moves between two positions with respect to a tray. The tray has inlet and outlet couplings which facilitate subjecting the interior of the cassette to vacuum and steam conditions as part of the sterilization process.

The first position of the lid is a closed position whereby the cassette interior is sealed from the outside when under vacuum or when sterile, either during the sterilization process or in a storage mode.

The second position of the lid occurs when the interior is pressurized and the lid is raised with respect to the tray. The seal still isolates the cassette interior from the outside even though the lid is not in the first or closed position.

The inlet and outlet couplings are configured to assure that once the instruments are sterilized, cassette removal from the sterilizing apparatus does not compromise the sterile cassette interior. This configuration utilizes valves and seals in each coupling, one set of seals positioned on the cassette exterior. The exterior seals isolate the interior of the cassette when the couplings are being disengaged from steam-supplying or evacuating probes of the sterilization apparatus. The exterior seals continue to isolate the sterile cassette interior from the outside until valves in the couplings close-for sealing purposes.

The inlet and outlet couplings also employ a pressure relief valve that allows release of unwanted pressure inside the cassette interior. The pressure relief valve also functions in concert with the other valve in the coupling to maintain vacuum conditions in the cassette interior once the sterilization process is complete. By maintaining such conditions, the instruments that have been sterilized can be stored for an extended period of time within the cassette. Thus, instruments can be sterilized ahead of time and stored until needed.

Figure 1:
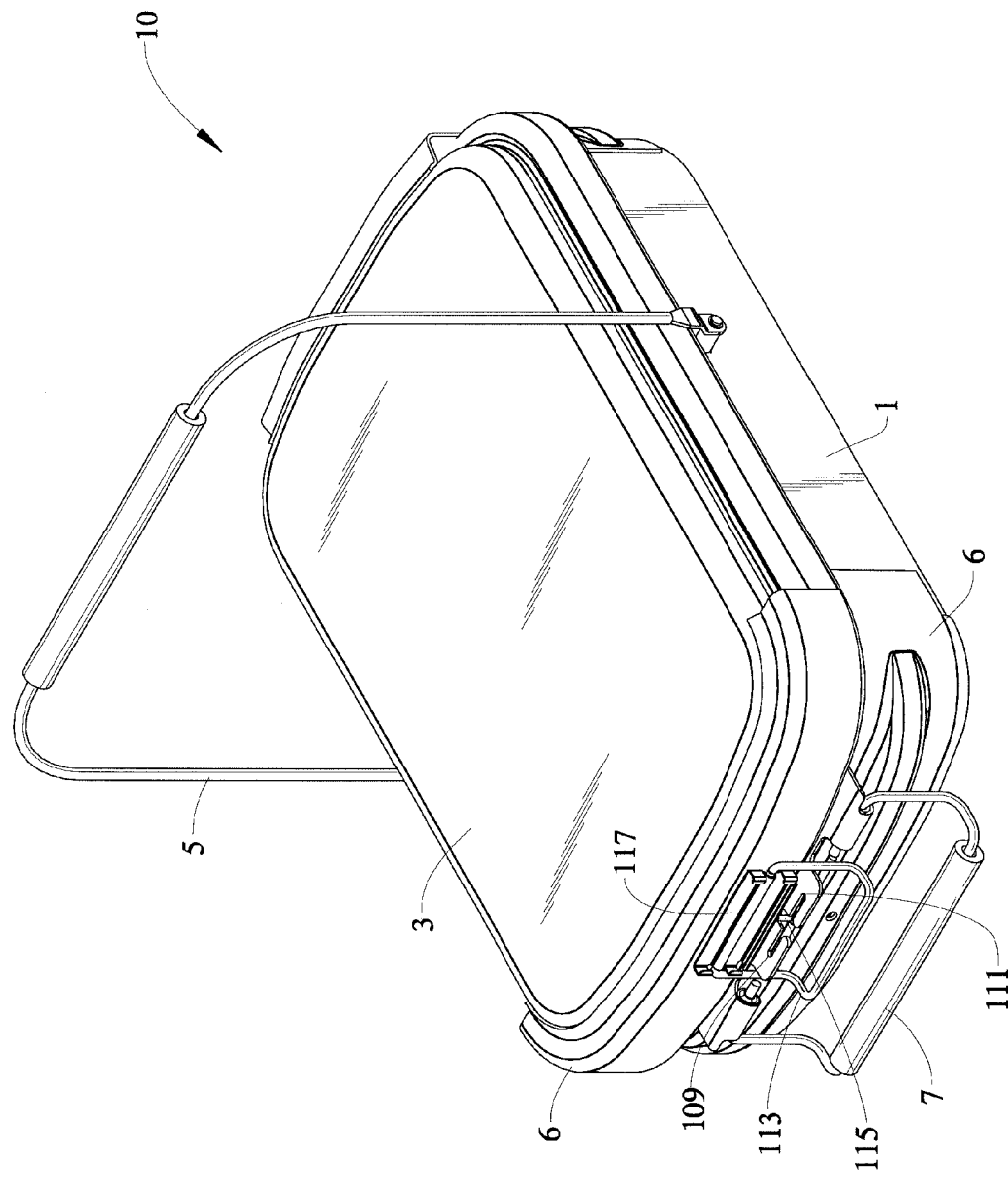
FIG. 1 is a front perspective view of one embodiment of the cassette of the invention.

FIG. 1 shows a preferred cassette embodiment 10 for storage of dental instruments, medical instruments, or the like. The cassette is comprised of two halves: a lower half hereafter referred to as "cassette tray" 1 and an upper half hereafter referred to as "cassette lid" 3. The cassette tray 1 is a container with a bottom and walls into which the instruments to be sterilized are placed and which remains stationary inside a sterilization apparatus throughout the entire sterilization cycle. The cassette 10 includes an auxiliary handle 5 shown in its carrying position and a front handle 7 shown in its resting position. A rear handle (not shown), which is of a similar design and construction to the front handle and which is located at the rear of the cassette, can also be realized. Both the cassette tray and the cassette lid are preferably constructed out of stainless steel or similar materials to facilitate heat transfer to the cassette contents during the sterilization cycle. Of course, other handle designs may be utilized to transport the cassette 10.

One inventive aspect of the cassette 10 lies in the fact that when used in conjunction with a sterilization apparatus and method that employs a structural chamber, hereafter referred to as an armature, the combined system is capable of withstanding both pressure and vacuum required for sterilization of dental and medical instruments. Yet at the same time, the lightweight cassette provides portability and sterile transport/storage of instruments. The preferred cassette embodiment functions under vacuum because the sterilization system draws a vacuum on both the cassette and the space created by the armature surrounding the cassette, resulting in a zero differential pressure between the cassette and the armature during all vacuum draws. The preferred cassette embodiment functions under pressure due to the fact that the cassette is transmitting most of the structural load to the structurally-superior armature during pressurization. Thus no undue stresses were exerted on the cassette itself during a sterilization cycle. This sterilization apparatus is disclosed in the Applicant's co-pending Canadian patent application no. 2,268,042. The cassette 10. is preferably constructed with reinforcing members or bumpers 6 on ends of both the tray 1 and the lid 3. The bumpers 6 provide additional structural support to the tray 1 and lid 3 in areas that are not in contact with the armature since these areas, unlike the top and bottom of the cassette, do not have additional support during the pressurization cycle of the sterilization process. The bumpers 6 are depicted as plates that are spot-welded or attached in other ways to the lid 3 and tray 1, Other forms of structural support could also be employed such as strengthening ribs in the walls of the lid and tray or the like.

The upside down cassette lid 3, as shown in FIG. 2, is connected via a conventional hinge 9 to the cassette tray 1 and is capable of moving vertically up or down with respect to the cassette tray depending on the pressure inside the cassette. The hinge tab 11 fits within a complementary-sized slot 8 in a flange 12 in the tray 1, see FIG. 5.

A tight seal is formed between the cassette lid 3 and cassette tray 1 via an end-user replaceable, bi-directional seal gland 13 installed on the inner lining of the cassette lid 3. The seal - 13 has a continuous form which surrounds the lid periphery.

Figure 3A:
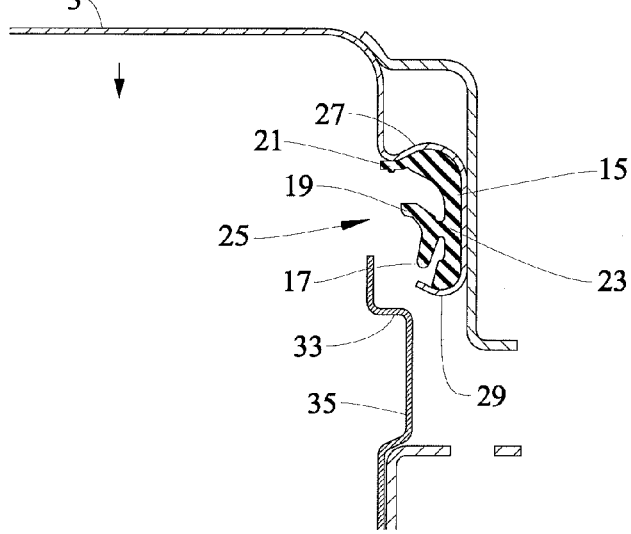
FIG. 3A is a partial cross sectional view of the lid and tray of the cassette in the open position.

FIG. 3A shows a cross-section of the bi-directional seal 13, which consists of a continuous seal body 15, a first lip 17, a second lip 19, and a third lip 21. The first lip 17 and the second lip 19 are connected to the main body 15 via the seal pivot member 23. The seal body 15 rests in a channel 25 having opposing walls; the third lip 21 resting against one of the walls 27. The other wall 29 protects the first lip 17 as described below.

When the cassette lid 3 is detached from the cassette tray 1 as shown in FIG. 3A (the open position), the first lip 17 is at its natural position, which is stowed completely behind the wall 29, thereby preventing the first lip 17 from being damaged during the closing of the cassette lid 3.

Figure 3B:
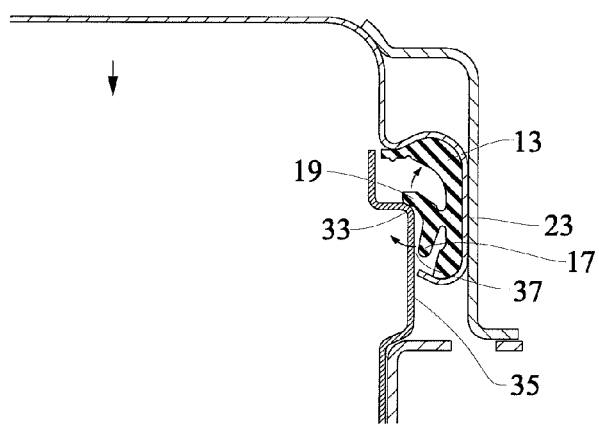
FIG. 3B is a partial cross sectional views of the lid and tray of FIG. 3A with the lid in an intermediate or partially closed position.
Figure 3C:
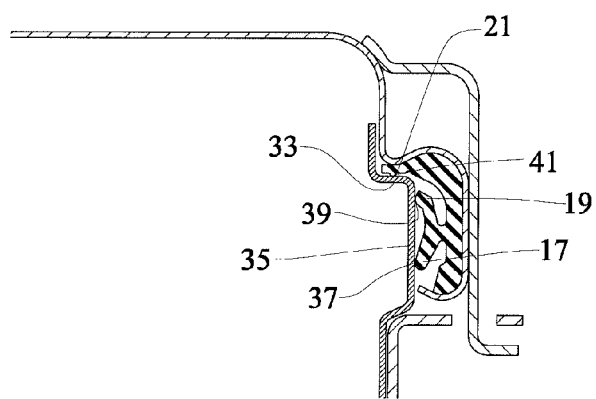
FIG. 3C is a partial cross sectional view of the lid and tray of FIG. 3A with the lid in a closed or vacuum/storage sealed condition.

During the closing of the cassette lid 3, the second lip 19 first comes into contact with the cassette tray surface 33, as shown in FIG. 3B. As the cassette lid 3 continues to travel downwards towards to the cassette tray 1, the second lip 19 rotates upwards and outwards about the seal pivot member 23, causing the first lip 17 to rotate upwards and inwards until it comes into contact with the cassette tray wall 35 to form a first seal 37. Further travel of the cassette lid 3 towards the cassette tray 1 causes the second lip 19 to also come into contact with the cassette tray wall 35, forming a second seal 39. Finally, the third lip 21 comes into contact with the cassette tray surface 33 to form a third and final seal 41 (the closed position), as shown in FIG. 3C.

Figure 4A:
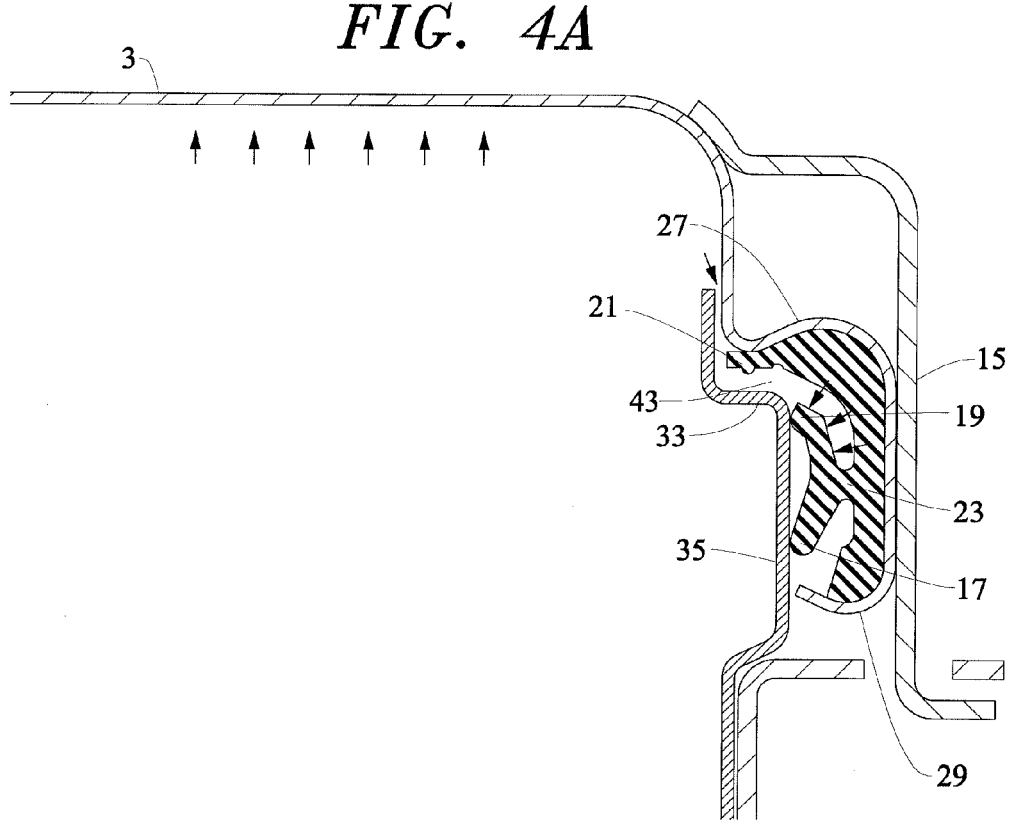
FIG. 4A shows the configuration of the seal when the cassette of FIG. 1 is pressurized.

During the pressurization phase of the sterilization cycle as shown in FIG. 4A, steam is injected into the cassette 10, causing the cassette lid 3 and seal 13 to move upwards and away from the cassette tray 1 until it comes into contact with and is stopped by an upper heating plate 44 situated in the armature of the sterilization apparatus (not shown). As the third lip 21 moves away from the cassette tray 3, a channel 43 is created between the seal body 15, including the seal lip 21, and the surface 33 of the tray 1 and the second lip 19. As pressurized steam enters the channel 43, the steam presses the second finger or pressure lip 19 against the cassette tray wall 35 thus preventing any leakage from occurring inside the cassette to the outside (the intermediate position).

The upward movement of the cassette lid 3 during pressurization also ensures good thermal contact between the stainless steel cassette lid 3 and the upper heating plate 44 situated in the armature (not shown), as well as between the stainless steel cassette tray 1 and the lower heating plate (also not shown). This facilitates the heat transfer from the heating plates to the cassette contents, thereby shortening the time it takes to bring the cassette contents to sterilization temperature.

Figure 4B:
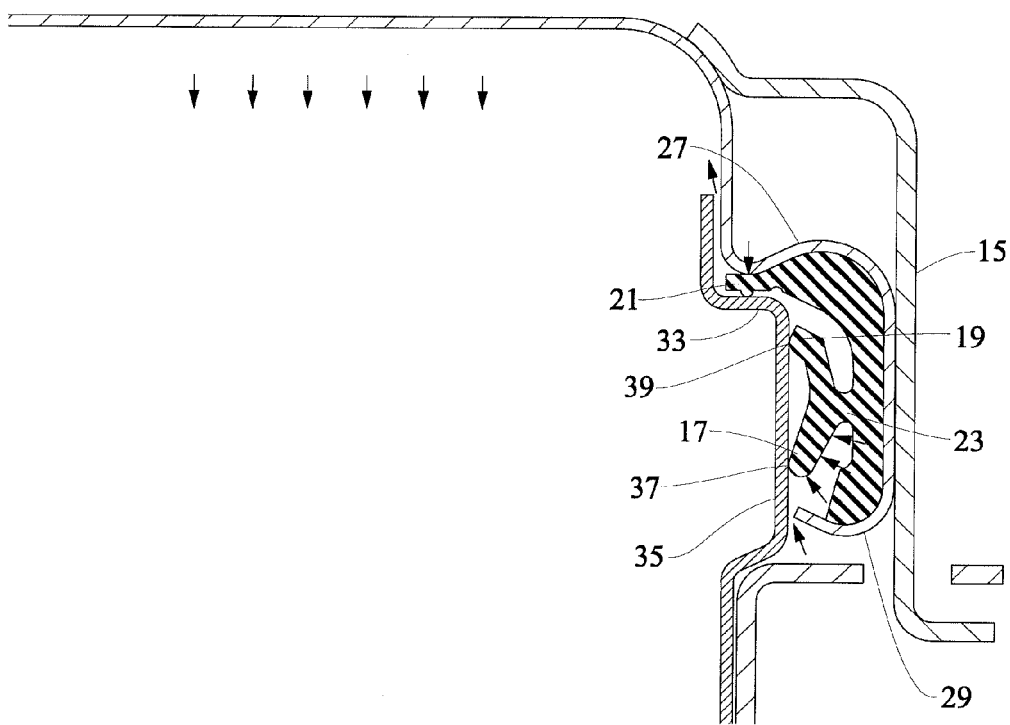
FIG. 4B shows the configuration of the seal when the cassette of FIG. 1 is under vacuum.

At the end of a sterilization cycle, as the hot air inside the cassette 10 cools down, its volume is reduced, thereby creating a vacuum inside the cassette, as shown in FIG. 4B. As a result, the cassette lid 3 is pulled towards the cassette tray 1. This in turn compresses the third lip 21 against the cassette tray surface 33 and pulls the first lip 17 inwards towards the cassette tray wall 35, thereby sealing the cassette 10 and preventing ambient air from entering into the cassette 10.

Another aspect of the inventive cassette involves an inlet and an outlet to allow for ingress and egress of steam, air, and the like as part of the steam sterilization process. In one embodiment, steam enters the cassette through a coupling in the cassette tray 1; hereafter referred to as the inlet coupling 45 and exits the cassette through another coupling of identical design in the cassette tray, hereafter referred to as the outlet coupling 47. The inlet and outlet couplings are mounted on the rear wall of the cassette tray as shown in FIG. 5. Although the couplings 45 and 47 are characterized as inlet and outlets, depending on the particular sterilization cycle taking place, both couplings could function as inlets or outlets. For example, during an evacuation cycle, each coupling 45 and 47 could be used as an outlet as described in Applicant's Canadian patent application mentioned above.

Figure 6:
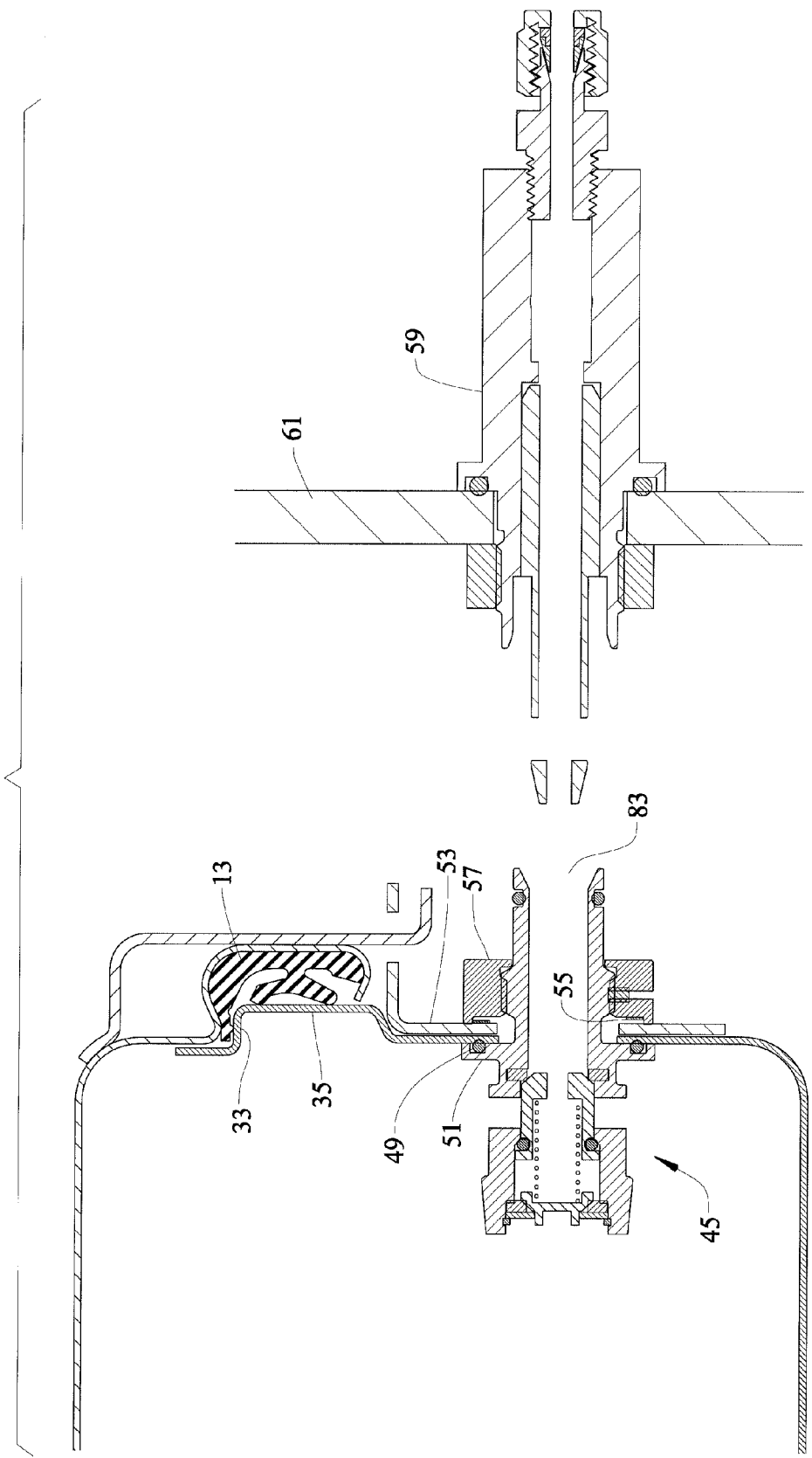
FIG. 6 is a cross sectional view of one of the couplings shown in FIG. 5 and a probe of a sterilization apparatus adapted -to interface with the coupling.

FIG. 6 shows a preferred coupling embodiment and the preferred mating probe embodiment of a sterilization system. Each coupling is attached to the cassette tray by means of an O-ring seal 49 placed between a coupling flange 51 and an inner rear wall 53 of the cassette tray 1. A wave spring 55 or a compression spring of similar design and a threaded nut 57 are employed to fasten the coupling 45 to the tray 1. When the nut 57 is tightened on the coupling 45, it compresses the wave spring 55 and the O-ring seal 49, thereby creating a leak-free attachment. At the same time this arrangement permits slight movements of the couplings 45 and 47 with respect to the cassette tray to permit self alignment of the couplings to a probe 59 during the insertion of the cassette into the armature (not shown), while maintaining the leak-free attachment. The probe 59 is mounted in a wall 61 of the sterilization apparatus (not shown) and provides communication between the interior of the tray 1 and the various media and processing used as part of the sterilization apparatus and methodology.

Figure 7A:
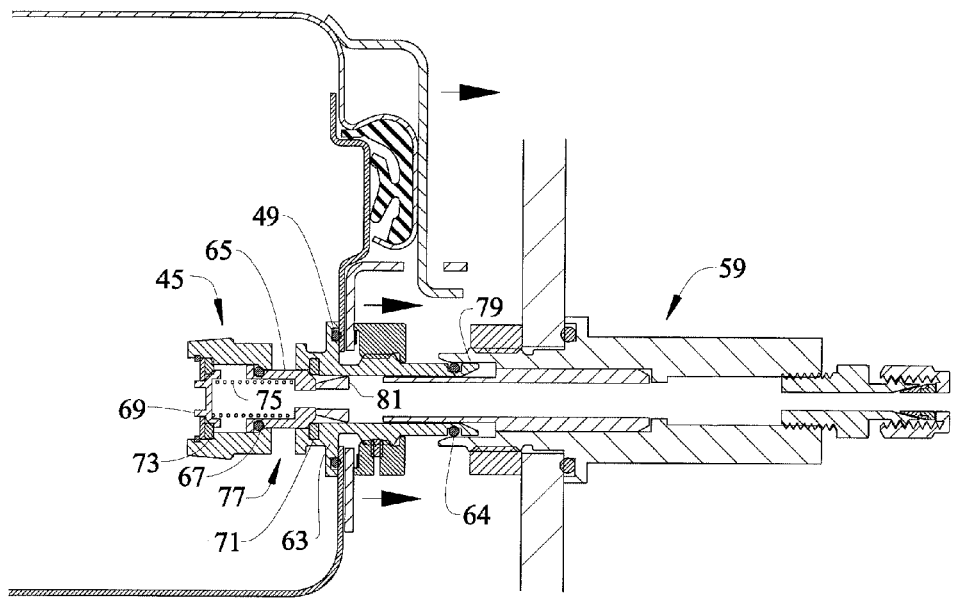
FIG. 7A is a cross sectional view of the coupling and probe of FIG. 6 with the cassette being inserted into the sterilization apparatus.

FIG. 7A shows the components of the coupling embodiment of FIG. 6, including a coupling body 63, a coupling O-ring 64, a front-poppet valve 65, a front-poppet valve O-ring 67, a rear-poppet valve 69, a front-poppet face seal 71, rear-poppet face seal 73 and a compression spring 75. In its natural state, the compression spring 75 forces the front-poppet valve 65 against the front-poppet face seal 71, the rear-poppet valve 69 against the rear-poppet face seal 73, and the front-poppet valve O-ring 67 against the coupling body 63. This arrangement seals openings 77 in the coupling, thereby isolating the cassette contents from the outside.

Figure 7B:
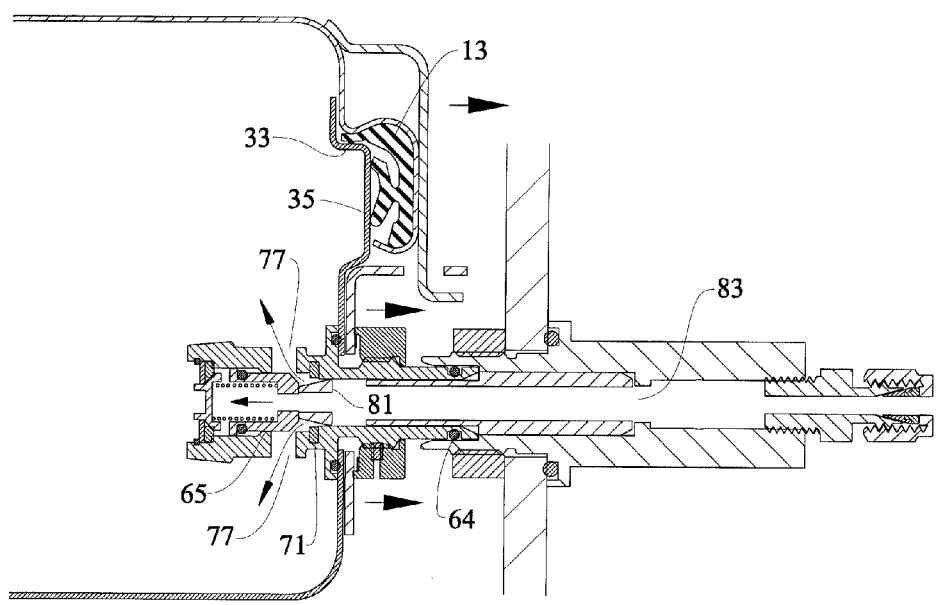
FIG. 7B shows the probe and coupling engaged to provide communication between the cassette interior and an interior of the probe.

Referring now to FIG. 7B, during the insertion of the cassette 10 into the armature, the coupling O-ring 64 first comes into contact with the inner surface 79 of each probe body 59, thereby creating a leak-free conduit between the cassette contents and the rest of the system as shown in FIG. 7A. Further travel of the cassette 10 causes the tapered probe tip 81 to come into contact with the front poppet valve 65, thereby pushing it away from the front-poppet face seal 71 by compressing the compression spring "75. The inward movement of the front-poppet valve 65 in the coupling 45 also unblocks the openings 77 in the coupling body 63. This creates a pathway between the cassette interior via the openings 77 in the coupling end positioned in the cassette interior and the open end 83 of the end of the coupling on the exterior of the cassette 10 (see FIG. 6). In addition, the cassette interior is then in communication with a sterilization system via the interior of the probe 59 for steam sterilization, purging, drying, and the like.

Figure 8:
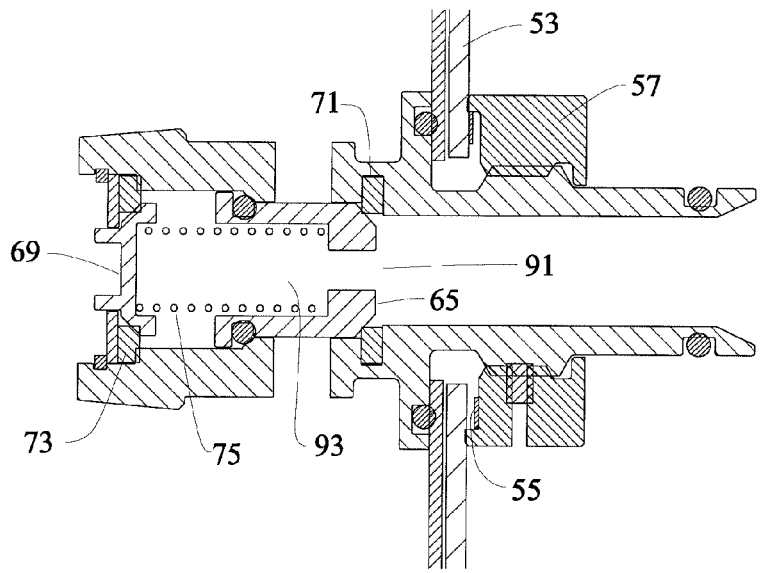
FIG. 8 shows the coupling of FIG. 6 with the pressure relief valve in operation.

The coupling 45 also serves as pressure relief device to allow proper closure of the cassette lid 3 and allow a pressurized cassette to be disengaged from the system in the event of a power failure and/or user intervention. Referring now to FIG. 8, during the closing of the cassette lid 3, the sealing is effective once the first lip 17 is in contact with the cassette tray wall 35, see FIG. 3B. The air inside the cassette 10 will resist any further closure of the cassette lid 3. The compression spring 75 in the coupling 45 is designed to overcome a predetermined cassette pressure. When the cassette pressure exceeds the predetermined limit, the compression spring 75 will be compressed, thereby allowing the rear-poppet valve 69 to move away from the rear-poppet face seal 73, thus creating a pathway for the cassette pressure to escape. This pressure relief property of the coupling also applies in the event of an interruption in sterilization cycle where the cassette is pressurized and the removal of the cassette is deemed desirable. The pressure relief device can be provided as a separate valve in the cassette wall, or as part of the coupling as described above.

The dual-poppet coupling design also permits sterile transport and storage of instruments in the cassette. When a sterilization cycle is completed, the cassette is detached from the probes 59 and disengaged from the system. Referring again to FIG. 7A, when the cassette is being withdrawn from the probe 59, the front poppet valve 65 returns to its natural position of sealing the openings 77 in the coupling while the coupling O-ring 64 is still engaged with the probe body surface 79. Thus, the sterile environment in the cassette 10 is not compromised during cassette removal. Upon disengagement of the coupling O-ring 64 from the probe body surface 79, the cassette contents have already been sealed by the closing action of the valve 65 to avoid recontamination.

As the stainless steel cassette is heated during the final drying phase of the sterilization cycle, the cassette is still warm to the touch when disengaging from the system. As the cassette cools down to ambient temperature, the volume of air inside the cassette decreases, resulting in a gradual build up of vacuum inside the cassette.

Figure 9:
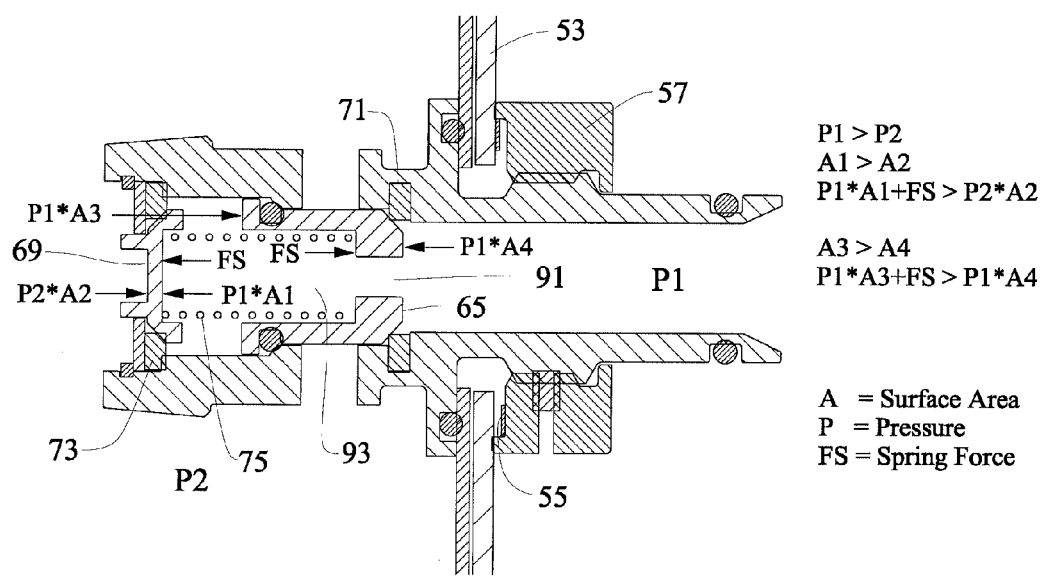
FIG. 9 shows the coupling of FIG. 6 in conjunction with a key detailing forces and pressures present during cassette use.

The aforementioned bi-directional seal as well as the couplings maintain this internal low vacuum. FIG. 9 shows how the dual-poppet coupling maintains the low vacuum created by the cooling of the cassette. As the pressure inside the cassette decreases due to cooling, the cassette pressure $P2$ is less than the ambient pressure $PI$. Since the front-poppet valve 65 has a center opening 91, the space between the front-and rear-poppet valves 93 also experiences pressure $PI$. The surface area of the rear-poppet valve facing the inside of the cassette, $A2$, is also smaller than the surface area of the rear-poppet valve facing the outside of the cassette, $A1$. Thus the force created by pressure $PI$ on surface area $A1$, i.e., $P1*A1$, is larger than that created by pressure $P2$ on surface area $A2$, i.e., $P2*A2$. With $P1*A1>P2*A2$ plus the additional force FS created by the compression spring, the rear-poppet valve 69 is pressed against the rear-poppet face seal 73 to prevent any air leakage from that interface. Similarly, since the surface area of the front-poppet valve 65 facing the cassette, $A3$, is larger than that of the front-poppet valve facing the ambient, $A4$; $P1*A3+FS>P1*A4$. Therefore, the front-poppet valve 65 is pressed against the front-poppet face seal 71 and the front-poppet valve O-ring 67 is pressed against the coupling body 63 to prevent any air leakage from this interface in order to achieve sterile storage and transport of instruments in the cassette.

In order to shorten the overall sterilization cycle, it is undesirable to have any condensate present inside the cassette since extra heat energy is required to heat up the extra, liquid water during the cycle. To ensure that no undue condensate is left behind in the cassette during the sterilization cycle, a modular cassette duct embodiment 100 is introduced into the cassette. The cassette duct embodiment 100 uses an elbow 101 made of silicone or similar autoclavable material and is attached to the outlet coupling in the cassette by protrusions 103 engaging recesses 105 in the coupling body 63. Other forms of attachment may be employed. A filter 107 can be attached to the bottom of the elbow 101 to prevent any debris from entering into the system during the condensate removal. The duct 100 is designed in such a way that it is close to, but does not touch the bottom of the cassette tray 1, in order to maximize the pathway or channel for the steam/water to travel to the coupling openings 77 yet be close enough to the cassette tray bottom 110 to allow suction to occur. The duct is removable by the end user for cleaning purpose. Both the cassette duct and the filter are replaceable by the end user.

FIG. 11 shows a preferred anti-tampering embodiment designed to prevent tampering of sterilized instruments. A self-adhesive, thermal-paper label (not shown) is inserted into a slot 109 in such a way that it covers the front portion of a preferably metal bracket 111. During the sterilization cycle, the color of the thermal paper is changed by the heat generated by the heating plates of the armature, indicating that the cassette has been placed in the chamber for sterilization. When the operator opens the cassette to retrieve the instruments, an opening handle 113 is lifted and a crossbar 115 tears the label, indicating that the cassette 10 has been opened. A label retainer 117 can store a label with relevant information displayed thereon. The cassette lid 3 could also include a conventional bar-code identification system to organize and identify the cassette contents electronically.

The invention also includes the bi-directional seal itself as well as a method of using the cassette in a sterilization process and apparatus employing vacuum for purging and steam sterilization. In these processes and apparatus, a steam sterilization cycle employs steam and vacuum for purging purposes. The inventive cassette is ideally adapted for such processes and apparatus since the cassette can function in a sealed manner during both vacuum and pressurized conditions. More particularly, the inventive method entails subjecting the cassette and the armature space surrounding it to a vacuum draw for pressure equalization between the two and air removal. Then, steam is used to purge air, the steam being removed using a vacuum again. The cassette is then pressurized and the instruments are subjected to steam sterilization conditions. The cassette pressure is then relieved, and the instruments are dried and any steam in the cassette is removed using vacuum. The cassette is then removed from the apparatus and either stored for later use of the instruments-, or the instruments are used immediately. The specific details of such processing are disclosed in Applicant's aforementioned Canadian patent application.

Although poppet valves have been disclosed to control ingress and egress of media to the interior of the cassette, other valve constructions could be used in conjunction with either the tray or lid to provide the necessary isolation of or access to the cassette interior during sterilization, storage or the like. Similarly, seal configurations other than o-rings may be employed to permit use of the cassette in the vacuum mode, pressure mode, and the storage mode.

While a pair of openings in the coupling body 63 are depicted for communication between the cassette interior and a sterilization apparatus, more or less opening could be employed. Similarly, while the openings are in the coupling body, other locations could be utilized. Further, while an elbow is disclosed as the duct for enhanced condensation pickup, other configurations may be employed depending on the orientation of the openings in the couplings situated within the cassette interior. The floating attachment of the couplings to the cassette tray is one embodiment of the invention but other floating configurations may be employed to allow engagement between couplings and probes of varying placement.

While the tray is described with the inlet and outlet and the lid is described as moving between the open, closed and intermediate or pressurized position, the tray could be designed to move between the various positions with the lid supporting the inlet and outlet. Similarly, the seal could be located on either the tray or lid.

As such, an invention has been disclosed in terms of preferred embodiments thereof which fulfills each and every one of the objects of the present invention as set forth above and provides new and improved cassette for use with sterilization apparatus and methods.

Of course, various changes, modifications and alterations from the teachings of the present invention may be contemplated by those skilled in the art without departing from the intended spirit and scope thereof. It is intended that the present invention only be limited by the terms of the appended claims.

What is claimed is:

1. A sterilization cassette comprising:
   a) a tray having at least an inlet and an outlet for connection to probes of a steam sterilization apparatus adapted to sterilize instruments contained in the cassette; and
   b) a lid attached to the tray, and
   c) a seal arranged between said lid and said tray, said lid, said tray and said seal forming a cassette interior capable of receiving said instruments and being sealed from the outside against passage of air or steam when the lid is in a closed position with respect to said tray and when the lid is in an intermediate position with respect to said tray, the lid being configured to provide an open position with respect to said tray to allow said instruments to be placed in or removed from said cassette interior, and said lid being configured to be held in said closed position with respect to said tray by pressure on the exterior of said cassette when the interior cassette pressure is less than the exterior cassette pressure, and said lid being configured to be held in said intermediate position with respect to said tray by pressure in the interior of said cassette when the interior cassette pressure is greater than the exterior cassette pressure, said lid being spaced from said tray when in said intermediate position further than when in said closed position, wherein the seal further comprises:
      i) a continuous seal body running along a periphery of the lid;
      ii) first and second lips extending from the seal body and pivotally linked thereto; and
      iii) a third lip extending from the seal body and spaced from the second lip to form a channel therebetween;
      iv) wherein the first and second lips provide sealing in the intermediate position and the first, second, and third lips provide sealing in the closed position;
   d) each of the inlet and the outlet openings having a coupling located therein to permit communication between the steam sterilization apparatus and the sterilization chamber.

2. The cassette of claim 1, wherein the lid has a channel along an inner surface thereof, the channel having opposing walls, the seal body arranged between the opposing walls with the first lip adjacent to one of the opposing walls and the third lip adjacent to the other of the opposing walls.

3. The cassette of claim 2, wherein one of the opposing walls extends from the inner surface a distance greater than a width formed by the first lip and the seal body to protect the first lip during closing and opening of the lid.

4. The cassette of claim 1, wherein the first and second lips are linked to the seal body by a member extending between the seal body and each of the first and second lips, the member providing a pivot point for movement of the first and second lips.

5. A sterilization cassette comprising:
   a) a tray having at least an inlet and an outlet for connection to probes of a steam sterilization apparatus adapted to sterilize instruments contained in the cassette; and
   b) a lid attached to the tray, and
   c) a seal arranged between said lid and said tray, said lid, said tray and said seal forming a cassette interior capable of receiving said instruments and being sealed from the outside against passage of air or steam when the lid is in a closed position with respect to said tray and when the lid is in an intermediate position with respect to said tray, the lid being configured to provide an open position with respect to said tray to allow said instruments to be placed in or removed from said cassette interior, and said lid begin configured to be held in said closed position with respect to said tray by pressure on the exterior of said cassette when the interior cassette pressure is less than the exterior cassette pressure, and said lid being configured to be held in said intermediate position with respect to said tray by pressure in the interior of said cassette when the interior cassette pressure is greater than the exterior cassette pressure, said lid being spaced from said tray when in said intermediate position further than when in said closed position;
   d) each of the inlet and the outlet openings having a coupling located therein to permit communication between the steam sterilization apparatus and the sterilization chamber, wherein each inlet and outlet coupling has a first valve to permit communication between the steam sterilization apparatus and the sterilization chamber, and a second valve to release excess pressure in the sterilization chamber, the first and second valves also sealing the sterilization chamber for storage of sterilized instruments when the said sterilization chamber is completely disengaged from the steam sterilization apparatus and wherein each of the inlet and outlet couplings further comprises a coupling body being sealably mounted in a wall of the tray with one end of the coupling body arranged outside of the sterilization chamber, and a second end arranged within the sterilization chamber, the one end having a first opening and the other end having at least one second opening, the first valve arranged in the coupling body, and the one end having a seal device on a peripheral surface thereof, the seal device spaced from the wall such that a seal is formed between the peripheral surface and a probe surface prior to opening or closing of the first valve to seal the sterilization chamber from ambient.

6. The cassette of claim 5, wherein the one end of the coupling body is tubular in shape and the seal device is an o-ring surrounding an outer surface of the tubular shape.

7. A sterilization cassette comprising:
 a) a tray having at least an inlet and an outlet for connection to probes of a steam sterilization apparatus adapted to sterilize instruments contained in the cassette; and
 b) a lid attached to the tray, and
 c) a seal arranged between said lid and said tray, said lid, said tray and said seal forming a cassette interior capable of receiving said instruments and being sealed from the outside against passage of air or steam when the lid is in a closed position with respect to said tray and when the lid is in an intermediate position with respect to said tray, the lid being configured to provide an open position with respect to said tray to allow said instruments to be placed in or removed from said cassette interior, and said lid begin configured to be held in said closed position with respect to said tray by pressure on the exterior of said cassette when the interior cassette pressure is less than the exterior cassette pressure, and said lid being configured to be held in said intermediate position with respect to said tray by pressure in the interior of said cassette when the interior cassette pressure is greater than the exterior cassette pressure, said lid being spaced from said tray when in said intermediate position further than when in said closed position;
 d) each of the inlet and the outlet openings having a coupling located therein to permit communication between the steam sterilization apparatus and the sterilization chamber, wherein each of the inlet and outlet couplings further comprises a coupling body being sealably mounted in a wall of the tray with one end of the coupling body arranged outside of the sterilization chamber, and a second end arranged within the sterilization chamber, the one end having a first opening and the other end having at least one second opening, the first valve arranged in the coupling body between the first and second openings, the first valve biased in a closed position, and adapted to be opened when a force is applied to a valve face against the bias, the second valve arranged in the coupling body and being biased in a closed position and movable to an open position upon application of a force applied from within the sterilization chamber.

8. The cassette of claim 7, wherein a spring is positioned between the first and second valves to provide the bias for closing each valve.

9. The cassette of claim 8, wherein the first valve has a bore providing communication between the first opening and the second valve so that when the sterilization chamber is under a vacuum for storage, the spring bias and atmospheric pressure maintains each of the first valve and the second valve in the closed position.

10. The cassette of claim 1, wherein each of the inlet and outlet further comprises a coupling body being sealably mounted in a wall of the tray with one end of the coupling body arranged outside of the sterilization chamber, and a second end arranged within the sterilization chamber, the one end having a first opening and the other end having at least one second opening, the first valve arranged in the coupling body, and the one end having a seal device on a peripheral surface thereof, the seal device spaced from the wall such that a seal is formed between the peripheral surface and a probe surface prior to opening or closing of the first valve to seal the sterilization chamber from ambient.

11. The cassette of claim 10, wherein the first valve is arranged in the coupling body between the first and second openings, is biased in a closed position, and adapted to be opened when a force is applied to a valve face against the bias, the second valve arranged in the coupling body and being biased in a closed position and movable to an open position upon application of a force applied from within the sterilization chamber.

12. The cassette of claim 11, wherein a spring is positioned between the first and second valves to provide the bias for closing each valve, and the first valve has a bore providing communication between the first opening and the second valve so that when the sterilization chamber is under a vacuum for storage, the spring bias and atmospheric pressure maintains each of the first valve and the second valve in the closed position.

13. The cassette of claim 12, further comprising a duct attached to the second end of the coupling body at one end thereof, with an opposite end of the duct positioned adjacent to the bottom of the tray to provide a channel for collection of condensate during steam sterilization of the instruments.

14. A sterilization cassette comprising:
 a) a tray having at least an inlet and an outlet for connection to probes of a steam sterilization apparatus adapted to sterilize instruments contained in the cassette; and
 b) a lid attached to the tray, and
 c) a seal arranged between said lid and said tray, said lid, said tray and said seal forming a cassette interior capable of receiving said instruments and being sealed from the outside against passage of air or steam when the lid is in a closed position with respect to said tray and when the lid is in an intermediate position with respect to said tray, the lid being configured to provide an open position with respect to said tray to allow said instruments to be placed in or removed from said cassette interior, and said lid begin configured to be held in said closed position with respect to said tray by pressure on the exterior of said cassette when the interior cassette pressure is less than the exterior cassette pressure, and said lid being configured to be held in said intermediate position with respect to said tray by pressure in the interior of said cassette when the interior cassette pressure is greater than the exterior cassette pressure, said lid being spaced from said tray when in said intermediate position further than when in said closed position;
 d) each of the inlet and the outlet openings having a coupling located therein to permit communication between the steam sterilization apparatus and the sterilization chamber, and
 further comprising a tamper indication device mounted on the cassette, the device including a heat sensitive material, the heat sensitive material indicating when the cassette has been heated for sterilization, the heat sensitive material mounted on one of the lid and the tray, and the device having a member mounted on the other of the lid and the tray, whereby separation of the lid and the tray causes the member to contact the heat sensitive material so as to indicate that the lid and tray have been opened.

15. A sterilization cassette comprising:
a) a tray having at least an inlet and an outlet for connection to probes of a steam sterilization apparatus adapted to sterilize instruments contained in the cassette; and
b) a lid attached to the tray, and
c) a seal arranged between said lid and said tray, said lid, said tray and said seal forming a cassette interior capable of receiving said instruments and being sealed from the outside against passage of air or steam when the lid is in a closed position with respect to said tray and when the lid is in an intermediate position with respect to said tray, the lid being configured to provide an open position with respect to said tray to allow said instruments to be placed in or removed from said cassette interior, and said lid begin configured to be held in said closed position with respect to said tray by pressure on the exterior of said cassette when the interior cassette pressure is less than the exterior cassette pressure, and said lid being configured to be held in said intermediate position with respect to said tray by pressure in the interior of said cassette when the interior cassette pressure is greater than the exterior cassette pressure, said lid being spaced from said tray when in said intermediate position further than when in said closed position;
d) each of the inlet and the outlet openings having a coupling located therein to permit communication between the steam sterilization apparatus and the sterilization chamber, wherein at least one of said inlet and outlet openings comprises a dual valve comprising first and second valves in a single coupling body, said first and second valves being biased to a closed position by a common biasing element and configured to open by application of a force against the bias.

16. A sterilization cassette comprising:
a) a tray having at least an inlet and an outlet for connection to probes of a steam sterilization apparatus adapted to sterilize instruments contained in the cassette; and
b) a lid attached to the tray, and
c) a seal arranged between said lid and said tray, said lid, said tray and said seal forming a cassette interior capable of receiving said instruments and being sealed from the outside against passage of air or steam when the lid is in a closed position with respect to said tray and when the lid is in an intermediate position with respect to said tray, the lid being configured to provide an open position with respect to said tray to allow said instruments to be placed in or removed from said cassette interior, and said lid begin configured to be held in said closed position with respect to said tray by pressure on the exterior of said cassette when the interior cassette pressure is less than the exterior cassette pressure, and said lid being configured to be held in said intermediate position with respect to said tray by pressure in the interior of said cassette when the interior cassette pressure is greater than the exterior cassette pressure, said lid being spaced from said tray when in said intermediate position further than when in said closed position;
d) each of the inlet and the outlet openings having a coupling located therein to permit communication between the steam sterilization apparatus and the sterilization chamber, and
wherein a portion of said seal is compressed between said lid and tray when said lid is in said closed position to prevent passage of air or steam and not compressed between said lid and said tray to allow passage of air or steam when in said intermediate position.

\* \* \* \* \*